(12) United States Patent
Luider et al.

(10) Patent No.: US 10,041,953 B2
(45) Date of Patent: Aug. 7, 2018

(54) MASS SPECTROMETRIC DETERMINATION OF DRUG RESISTANCE

(71) Applicant: Erasmus University Medical Center Rotterdam, Rotterdam (NL)

(72) Inventors: Theo Marten Luider, Rotterdam (NL); Wilhelmus Hubertus Francisus Goessens, Rotterdam (NL)

(73) Assignee: ERASMUS UNIVERSITY MEDICAL CENTER ROTTERDAM (NL)

( * ) Notice: Subject to any disclaimer, the term of this patent is extended or adjusted under 35 U.S.C. 154(b) by 0 days.

(21) Appl. No.: 14/782,111

(22) PCT Filed: Apr. 4, 2013

(86) PCT No.: PCT/NL2013/050255
§ 371 (c)(1),
(2) Date: Oct. 2, 2015

(87) PCT Pub. No.: WO2014/163487
PCT Pub. Date: Oct. 9, 2014

(65) Prior Publication Data
US 2016/0054332 A1 Feb. 25, 2016

(51) Int. Cl.
*G01N 33/68* (2006.01)
*C12Q 1/18* (2006.01)
*C12Q 1/37* (2006.01)

(52) U.S. Cl.
CPC ........... *G01N 33/6848* (2013.01); *C12Q 1/18* (2013.01); *C12Q 1/37* (2013.01); *G01N 2458/15* (2013.01); *G01N 2560/00* (2013.01); *G01N 2800/50* (2013.01)

(58) Field of Classification Search
CPC .................................................. G01N 33/6848
See application file for complete search history.

(56) References Cited

U.S. PATENT DOCUMENTS

| 6,120,986 | A | 9/2000 | Martin |
| 8,293,496 | B2 | 10/2012 | Govorun et al. |
| 8,580,535 | B2 | 11/2013 | Govorun et al. |
| 2005/0089947 | A1 | 4/2005 | Black et al. |
| 2008/0009029 | A1 | 1/2008 | Govorun et al. |
| 2011/0012016 | A1 | 1/2011 | Maier et al. |
| 2011/0245105 | A1 | 10/2011 | Citri |

FOREIGN PATENT DOCUMENTS

| CN | 102033102 A | 4/2011 |
| CN | 103003699 A | 3/2013 |
| DE | 102006021493 A1 | 11/2007 |
| DE | 102009033368 A1 | 1/2011 |
| GB | 2438066 A | 11/2007 |
| WO | WO03/087834 | 10/2003 |
| WO | 2010067358 A2 | 6/2010 |
| WO | WO2012/023845 | 2/2012 |

OTHER PUBLICATIONS

Hooff et al. J of Proteome Research, 2012, 11:79-84.*
Rosenkrands et al. J of Bacteriology, 2002, 3485-3491.*
Camare et al. Anal Bioanal Chem., 2007, 389:1633-1638.*
Stachyra et al. Antimicrobial Agents and Chemotherapy, 54(12):5132-5138.*
International Search Report dated Dec. 11, 2013 from corresponding PCT Application No. PCT/NL2013/050255.
Wilcox et al., "Single Ribosomal Protein Mutations in Antibiotic-Resistant Bacteria Analyzed by Mass Spectrometry," Antimicrobial Agents and Chemotherapy, 45:3046-3055 (2001).
Liesener and Karst, "Monitoring enzymatic conversions by mass spectrometry: a critical review", Anal Bioanal Chem., 382(7), pp. 1451-64, Aug. 2005 (Aug. 2005).
Gao et al., "Novel fluorogenic substrates for imaging beta-lactamase gene expression", J Am Chem Soc., 125(37), pp. 11146-7, Sep. 2003 (Sep. 2003).
Ji et al., "Identification of Streptothricin class antibiotics in the early stage of antibiotics screening by electrospray ionization mass spectrometry", Journal of Antibiotics, 61(11): 660-667, 2008.
Neu, "Relation of structural properties of beta-lactam antibiotics to antibacterial activity", 1995, The American J of Medicine, vol. 79, Supplement 2.
Rathore et al., "Extending matrix-assisted laser desorption/ionization triple quadruple mass spectrometry enzyme screening assays to targets with small molecule substrates", Rapid Communications in Mass Spectrometry, 23:3293-3300, 2009.
Cohen et al., "Small molecule analysis by MALDI mass spectrometry", Anal. Bioanal. Chem., 2002, 373:571-586.
"Overview of Affinity Purification", downloaded from https://www.thermofisher.com/us/en/home/life-science/protein-biology/protein-biology-learning-center/protein-biology-resource-library/pierce-protein-methods/overview-affinity-purification.html; pp. 1-9, Sep. 12, 2017.
Saves et al., "Mass spectral kinetic study of acylation and deacylation during the hydrolysis of penicillins and cefotaxime by beta-lactamase TEM-1 and the G238S mutant", Biochemistry, vol. 34, No. 37, 1995, pp. 11660-11667.
Aplin et al, "Use of electrospray mass spectrometry to directly observe an acyl enzyme intermediate in beta-lactamase catalysis", Febs Letters, Elsevier, vol. 277, No. 1-2, 1990, pp. 212-214.
Fenselau et al., "Identification of lactamase in antibiotic-resistant bacillus cereus spores", Applied and Environmental Microbiology, vol. 74, No. 3, 2007, pp. 904-906.
Keseru et al., "Identification of beta-lactamases in human and bovine isolates of *Staphylococcus aureus* strains having borderline resistance to penicillinase-resistant penicilians (PRPs) with proteomic methods", Veterinary Microbiology, Elsevier, vol. 147, No. 1-2, 2011, pp. 96-102.

(Continued)

*Primary Examiner* — Bin Shen
(74) *Attorney, Agent, or Firm* — McDermott Will & Emery LLP (57) ABSTRACT

The invention relates to a method to determine drug resistance in microbes. The method relates to measuring the drug resistance conferring protein by mass spectrometry. The mass spectrum acquired provides information whether an drug resistance conferring protein is present and information on the type of drug resistance conferring protein, on mutations of the drug resistance conferring protein as well as on the expression level of this protein.

10 Claims, 5 Drawing Sheets

(56) References Cited

OTHER PUBLICATIONS

Yazawa K et al., "Inactivation of Kanamycin A by phosphorylation in pathogenic nocardia", Microbiology and Immunology, vol. 35, No. 1, 1991, pp. 39-48, XP009144264.

Mosher et al., "Inactivation of chloramphenicol by O-phosphorylation: A novel resistance mechanism in streptomyces venezuelae ISP5230, A chloramphenicol producer" Journal of Biological Chemistry, vol. 270, No. 45, 1995, pp. 27000-27006.

Ikryannikova et al., "A MALDI TOF MS-based minisequencing method for rapid detection of TEM-type extended-spectrum beta-Lactamases in clinical strains of enterobacteriaceae", Journal of Microbiological Methods, vol. 75, No. 3, 1 Dec. 2008, pp. 385-391.

Dargis et al., "Use of biotinylated beta-lactams and chemiluminescence for studying of penicillin-binding proteins in bacteria", Antimicrobial Agents and Chemotherapy, May 1994, pp. 973-980.

Ohkawa et al., "Detection of beta-Lactamase-producing Bacteria from Female Patients with Acute Uncomplicated Cystitis", Proceedings of Urology, Nov. 1987, vol. 33, No. 11, pp. 1800-1805.

Niu et al., "SanJ, an ATP-dependent picolinate-CoA ligase, catalyzes the conversion of picolinate to picolinate-CoA during nikkomycin biosynthesis in Streptomyces ansochromogenes", Metab. Eng., May 2006, vol. 8, No. 3, pp. 183-195.

Welling et al., "Determination of enzyme activity by high-performance liquid chromatography", J. Chromatogr. B. Biomed. Appl., Sep. 1994, vol. 659, No. 1-2, pp. 209-225.

Lewis et al., "A point mutation leads to altered product specificity in beta-lactamase catalysis", Proc. Natl. Acad. Sci. USA, Jan. 1997, vol. 94, No. 2, pp. 443-447.

Ling et al., "Research Progress on extended-spectrum beta lactamase-producing Gram-negative bacteria", Chinese Journal of Nosocomiology, 2008, vol. 18, No. 6, pp. 897-900.

Hassing et al., "Detection of amino acid substitutions in the GyrA protein of fluoroquinolone-resistant typhoidal *Salmonella* isolates using high-resolution mass spectrometry", Int J Antimicrob Agents. May 2016;47(5), pp. 351-356.

Monteferrante et al., "Evaluation of different pretreatment protocols to detect accurately clinical carbapenemase-producing enterobacteriaceae by MALDI-TOF", J Antimicrob Chemother. Oct. 2016;71(10), pp. 2856-2867.

Goodenough, "High resolution mass spectrometry approaches for the quantitation of proteins using stable isotopically labeled peptides", The review of American Pharmaceutical Business and Technology, 2011, pp. 1-13.

Lewis et al., "Identification of viral mutants by mass spectrometry", Proc. Natl. Acad. Sci. U.S.A., 1998, 95, 8596-8601.

* cited by examiner

>gi|17865733|sp|P37411.3|GYRA_13471 RecName: Full=DNA gyrase subunit A

SEQ ID NO 5:

MSDLAREITPVNIEEELKSSYLDYAMSVIVGRALPDVRDGLKPVHRRVLYAMNVLGNDWN

KAYKKSARVVGDVIGKYHPHGDSAVYDTIVRMAQPFSLRYMLVDGQGNFGSIDGDSAAAM

RYTEIRLAKIAHELMADLEKETVDFVDNYDGTEKIPDVMPTKIPNLLVNGSSGIAVGMAT

NIPPHNLTEVINGCLAYIDNEDISIEGLMEHIPGPDFPTAAIINGRRGIEEAYRTGRGKV

YIRARAEVEADAKTGRETIIVHEIPYQVNKARLIEKIAELVKDKRVEGISALRDESDKDG

MRIVIEVKRDAVGEVVLNNLYSQTQLQVSFGINMVALHHGQPKIMNLKDIISAFVRHRRE

VVTRRTIFELRKARDRAHILEALAIALANIDPIIELIRRAPTPAEAKAALISRPWDLGNV

AAMLERAGDDAARPEWLEPEFGVRDGQYYLTEQQAQAILDLRLQKLTGLEHEKLLDEYKE

LLEQIAELLHILGSADRLMEVIREEMELIRDQFGDERRTEITANSADINIEDLISQEDVV

VTLSHQGYVKYQPLTDYEAQRRGGKGKSAARIKEEDFIDRLLVANTHDTILCFSSRGRLY

WMKVYQLPEASRGARGRPIVNLLPLEANERITAILPVREYEEGVNVFMATASGTVKKTAL

TEFSRPRSAGIIAVNLNDGDELIGVDLTSGSDEVMLFSAAGKVVRFKEDAVRAMGRTATG

VRGIKLAGDDKVVSLIIPRGEGAILTVTQNGYGKRTAADEYPTKSRATQGVISIKVTERN

GSVVGAVQVDDCDQIMMITDAGTLVRTRVSEISVVGRNTQGVILIRTAEDENVVGLQRVA

EPVDDEELDAIDGSVAEGDEDIAPEAESDDDVADDADE

Fig. 3

>gi|17865733|sp|P37411.3|GYRA_17109 RecName: Full=DNA gyrase subunit A

SEQ ID NO: 6

MSDLAREITPVNIEEELKSSYLDYAMSVIVGRALPDVRDGLKPVHRRVLYAMNVLGNDWN
KAYKKSARVVGDVIGKYHPHGDYAVYDTIVRMAQPFSLRYMLVDGQGNFGSIDGDSAAAM
RYTEIRLAKIAHELMADLEKETVDFVDNYDGTEKIPDVMPTKIPNLLVNGSSGIAVGMAT
NIPPHNLTEVINGCLAYIDNEDISIEGLMEHIPGPDFPTAAIINGRRGIEEAYRTGRGKV
YIRARAEVEADAKTGRETIIVHEIPYQVNKARLIEKIAELVKDKRVEGISALRDESDKDG
MRIVIEVKRDAVGEVVLNNLYSQTQLQVSFGINMVALHHGQPKIMNLKDIISAFVRHRRE
VVTRRTIFELRKARDRAHILEALAIALANIDPIIELIRRAPTPAEAKAALISRPWDLGNV
AAMLERAGDDAARPEWLEPEFGVRDGQYYLTEQQAQAILDLRLQKLTGLEHEKLLDEYKE
LLEQIAELLHILGSADRLMEVIREEMELIRDQFGDERRTEITANSADINIEDLISQEDVV
VTLSHQGYVKYQPLTDYEAQRRGGKGKSAARIKEEDFIDRLLVANTHDTILCFSSRGRLY
WMKVYQLPEASRGARGRPIVNLLPLEANERITAILPVREYEEGVNVFMATASGTVKKTAL
TEFSRPRSAGIIAVNLNDGDELIGVDLTSGSDEVMLFSAAGKVVRFKEDAVRAMGRTATG
VRGIKLAGDDKVVSLIIPRGEGAILTVTQNGYGKRTAADEYPTKSRATQGVISIKVTERN
GSVVGAVQVDDCDQIMMITDAGTLVRTRVSEISVVGRNTQGVILIRTAEDENVVGLQRVA
EPVDDEELDAIDGSVAEGDEDIAPEAESDDDVADDADE

Fig 4 gi|17865733|sp|P37411.3|GYRA_6838 RecName: Full=DNA gyrase subunit A

SEQ ID NO: 7

MSDLAREITPVNIEEELKSSYLDYAMSVIVGRALPDVRDGLKPVHRRVLYAMNVLGNDWN

KAYKKSARVVGDVIGKYHPHGDFAVYGTIVRMAQPFSLRYMLVDGQGNFGSIDGDSAAAM

RYTEIRLAKIAHELMADLEKETVDFVDNYDGTEKIPDVMPTKIPNLLVNGSSGIAVGMAT

NIPPHNLTEVINGCLAYIDNEDISIEGLMEHIPGPDFPTAAIINGRRGIEEAYRTGRGKV

YIRARAEVEADAKTGRETIIVHEIPYQVNKARLIEKIAELVKDKRVEGISALRDESDKDG

MRIVIEVKRDAVGEVVLNNLYSQTQLQVSFGINMVALHHGQPKIMNLKDIISAFVRHRRE

VVTRRTIFELRKARDRAHILEALAIALANIDPIIELIRRAPTPAEAKAALISRPWDLGNV

AAMLERAGDDAARPEWLEPEFGVRDGQYYLTEQQAQAILDLRLQKLTGLEHEKLLDEYKE

LLEQIAELLHILGSADRLMEVIREEMELIRDQFGDERRTEITANSADINIEDLISQEDVV

VTLSHQGYVKYQPLTDYEAQRRGGKGKSAARIKEEDFIDRLLVANTHDTILCFSSRGRLY

WMKVYQLPEASRGARGRPIVNLLPLEANERITAILPVREYEEGVNVFMATASGTVKKTAL

TEFSRPRSAGIIAVNLNDGDELIGVDLTSGSDEVMLFSAAGKVVRFKEDAVRAMGRTATG

VRGIKLAGDDKVVSLIIPRGEGAILTVTQNGYGKRTAADEYPTKSRATQGVISIKVTERN

GSVVGAVQVDDCDQIMMITDAGTLVRTRVSEISVVGRNTQGVILIRTAEDENVVGLQRVA

EPVDDEELDAIDGSVAEGDEDIAPEAESDDDVADDADE

Fig 5 gi|17865733|sp|P37411.3|GYRA_19222 RecName: Full=DNA gyrase subunit A

SEQ ID NO: 8

MSDLAREITPVNIEEELKSSYLDYAMSVIVGRALPDVRDGLKPVHRRVLYAMNVLGNDWN
KAYKKSARVVGDVIGKYHPHGDFAVYDTIVRMAQPFSLRYMLVDGQGNFGSIDGDSAAAM
RYTEIRLAKIAHELMADLEKETVDFVDNYDGTEKIPDVMPTKIPNLLVNGSSGIAVGMAT
NIPPHNLTEVINGCLAYIDNEDISIEGLMEHIPGPDFPTAAIINGRRGIEEAYRTGRGKV
YIRARAEVEADAKTGRETIIVHEIPYQVNKARLIEKIAELVKDKRVEGISALRDESDKDG
MRIVIEVKRDAVGEVVLNNLYSQTQLQVSFGINMVALHHGQPKIMNLKDIISAFVRHRRE
VVTRRTIFELRKARDRAHILEALAIALANIDPIIELIRRAPTPAEAKAALISRPWDLGNV
AAMLERAGDDAARPEWLEPEFGVRDGQYYLTEQQAQAILDLRLQKLTGLEHEKLLDEYKE
LLEQIAELLHILGSADRLMEVIREEMELIRDQFGDERRTEITANSADINIEDLISQEDVV
VTLSHQGYVKYQPLTDYEAQRRGGKGKSAARIKEEDFIDRLLVANTHDTILCFSSRGRLY
WMKVYQLPEASRGARGRPIVNLLPLEANERITAILPVREYEEGVNVFMATASGTVKKTAL
TEFSRPRSAGIIAVNLNDGDELIGVDLTSGSDEVMLFSAAGKVVRFKEDAVRAMGRTATG
VRGIKLAGDDKVVSLIIPRGEGAILTVTQNGYGKRTAADEYPTKSRATQGVISIKVTERN
GSVVGAVQVDDCDQIMMITDAGTLVRTRVSEISVVGRNTQGVILIRTAEDENVVGLQRVA
EPVDDEELDAIDGSVAEGDEDIAPEAESDDDVADDADE

MASS SPECTROMETRIC DETERMINATION OF DRUG RESISTANCE

RELATED APPLICATIONS

This application is the U.S. National Stage of International Application No. PCT/NL2013/050255, filed Apr. 4, 2013, published in English, the entire teachings of the above application is incorporated herein by reference.

The invention relates to a method to determine drug resistance in microbes. The method relates to measuring a drug resistance conferring protein by mass spectrometry. The mass spectrum acquired provides information whether a drug resistance conferring protein, is present and information on the type of drug resistance conferring protein as well as on mutations in the drug resistance conferring protein.

BACKGROUND

Resistance to drugs of microbes poses an increasing problem to the health care system. Resistant microbes, such as bacteria and unicellular fungi, but also viruses, may complicate the treatments of infections in critically ill patients, especially in surgery, hemato-oncology and intensive care in general. Microbial isolates that are resistant to more than one, and even to all available drugs are also known. Especially multi-resistant bacteria that are resistant to almost all antibiotics are a problem. It is therefore important to have a fast and accurate method to establish whether a microbe is resistant to a drug and even more important to which kind of drug, this is especially the case for antibiotic resistant bacteria. A quick and accurate determination of the kind of resistance is vital for the choice of antimicrobial therapy. It is also important to treat the microbes as specifically as possible to avoid further development of resistance. Therefore, routine microbial laboratories need fast and reliable methods to detect resistance in microorganism and establish the kind and preferably also the degree of resistance against a drug.

Most current techniques for susceptibility determinations of microorganisms are laborious and time-consuming as they encompass the growing of the microorganism. Also genetic tests are available to detect known resistance genes in the genome of the pathogen. The drawbacks of the genetic testing is that one will only find what one is looking for, as specific primers are required for known resistance genes. If for another resistance, no primers are used or available, this resistance gene will not be identified. Furthermore, a resistance gene may be present, but may not be expressed or to a low level. This will lead to a positive identification of resistance while the microorganism is not resistant e.g. the gene for a chromosomal encoded AmpC β-lactamase in *E. coli* may be present but the microorganism may still be susceptible to ampicillin because the gene is not expressed or only expressed to a low level.

Mass spectrometry has been used to identify and type microorganism. In recent years MALDI-TOF MS has been used to measure protein profiles of microorganism. Mass spectra are acquired and compared to a database of reference mass spectra of microorganisms where after software-assisted search the identification of microorganism is determined (U.S. Pat. No. 8,293,496). The advantages of such a system are fast determination of the microorganism, i.e. approximately 2 minutes vs 6-8 hours with phenotypical determination, and whole microorganism may be used so no need for further purification steps. About 84%-95% of clinical isolates tested were identified correctly with MALDI-TOF MS (Eigner et al (2009) din Lab 55(7-8):289-296; Seng et al (2009) Clin Infect Dis 49(4):543-551). The drawback is that in the range of measurement, usually between 3-11 kDa, ribosomal protein are predominantly identified, and the resistance may not relate directly to ribosomal proteins. In addition, with the MALDI-TOF techniques of the prior art, mutations in drug target proteins may not be detected. In addition, with the MALDI-TOF technique as used in the prior art, one is dependent on reference spectra, if no reference spectrum is present in the database, then the microorganism cannot be identified or will be wrongly identified. The strength of the method therefore depends on the quality of the database. Furthermore, with the current MALDI-TOF technique, one cannot distinguish between different drug conferring proteins within the same class. For instance, one may determine the presence of a beta-lactamase, but not which kind of beta-lactamase. In view of the fact that more than 900 different kinds of beta-lactamases are known, it may not be sufficient if one does not know which kind of beta-lactamase is present.

There is a need to optimize the detection of drug resistant microorganisms in a fast and reliable way. There is also a need to specifically identify the type of resistance, or even to identify the mutation conferring resistance or expression level of the resistance conferring protein.

SUMMARY OF THE INVENTION

The present invention is directed to a method to detect resistance of microorganism to a antimicrobial drug said method comprising the steps:
  (a) digesting a sample of a microorganism with an endoprotease, resulting in a mix of peptides
  (b) acquiring a mass spectrum of the mix of peptides from step a)
  (c) determining the resistance of the microorganism.

The present invention is further directed to a kit of parts for characterizing the drug resistance of a microorganism comprising:
  (a) a lysis agent for lysing a microorganism;
  (b) an endoprotease
  (c) a MS matrix material.

DETAILED DESCRIPTION

DEFINITIONS

The term drug or antimicrobial drug as used herein refers to any kind of drug that is directed to decrease the viability of a microbe/microorganims, or which inhibits the growth or production of a microbe/microorganism Inhibits the growth or reproduction" means increasing the generation cycle time by at least 2-fold, preferably at least 10-fold, more preferably at least 100-fold, and most preferably indefinitely, as in total cell death or complete inhibition of the microbe/ microorganism. As used in this disclosure, an antimicrobial drug is further intended to include an antibiotic, antiviral, antifungal or antiparasitic. Non-limiting examples of antimicrobial drugs are penicillins, protease inhibitors, nucleoside analogues, imidazole, benzoic acid, antinematodes, or antiprotozoals.

The terms "antibiotic" is used herein to describe a compound or composition which decreases the viability of a microorganism, or which inhibits the growth or reproduction of a microorganism. "Inhibits the growth or reproduction" means increasing the generation cycle time by at least 2-fold, preferably at least 10-fold, more preferably at least 100-fold, and most preferably indefinitely, as in total cell death. As used in this disclosure, an antibiotic is further intended to include an antibacterial, bacteriostatic, or bactericidal agent. Non-limiting examples of antibiotics useful in aspect of the invention include penicillins, cephalosporins, aminoglycosides, sulfonamides, macrolides, tetracyclins, lincosamides, quinolones, chloramphenicol, glycopeptides, metronidazole, rifampin, isoniazid, ethambutol, pyrazinamide, spectinomycin, folate inhibitors, sulfamethoxazole, and others.

The term antiviral drug as used herein refers to a class of drugs used specifically for treating viral infections and may include virucides. A virucide is an agent (physical or chemical) that deactivates or destroys viruses. Antiviral drugs may also inhibit the development and/or production of the virus. Non-limiting examples of classes of antiviral drugs are viral entry inhibitors, viral uncoating inhibitors, viral transcription inhibitors, viral integrase inhibitors, viral protease inhibitors, and/or inhibitors of the viral release phase. Non-limiting examples of specific antiviral drugs are zanamivir, oseltamivir, rifampicin, phosphorothioate antisense drug, acyclovir, zidovudine (AZT), lamivudine, saquinavir, ritonavir, indinavir, nelfinavir, amprenavir, Boceprevir, Telaprevir, tenofovir, adefovir, efavirenz, nevirapine, delavircline, etravidine, rilpivirine, amantadine, rimantadine, or pleconaril.

The term antifungal refers to a class of drugs used to treat fungal infections and/or to pharmaceutical fungicides. Fungal infection are for example but not limited to mycoses, candidiasis, athletes's food, Dermatophytosis (ringworm), cryptococcal meningitis. Non-limiting examples of classes of antifungal drugs are polyene antifungals, azole antifungals (imidazole, triazole, thiazole), allylamines, or echinocanclins. Non-limiting examples of specific antifungal drugs are Amphotericin B, Candicidin, Filipin, Hamycin, Natamycin, Nystatin, Rimocidin, Bifonazole, Butoconazole, Clotrimazole, Econazole, Fenticonazole, Isoconazole, Ketoconazole, Miconazole, Omoconazole, Oxiconazole, Sertaconazole, Sulconazole, Tioconazole, Albaconazole, Fluconazole, Isavuconazole, Itraconazole, Posaconazole, Ravuconazole, Terconazole, Voriconazole, Abafungin, Amorolfin, Butenafine, Naftifine, Terbinafine, Anidulafungin, Caspofungin, Micafungin, Benzoic acid, Ciclopirox, Flucytosine, Griseofulvin, Haloprogin, Polygodial, Tolnaftate, Undecylenic acid or Crystal violet.

The term antiparasitic is used for a class of drugs which are indicated for the treatment of parasitic diseases such as nematodes, cestodes, trematodes, infectious protozoa, and amoebas. Non-limiting examples of classes of antiparasitic drugs are antinematodes, anticestodes, antitrematodes, antiamoebics, antiprotozoals. Non-limiting examples of specific antiparasitic drugs are, Mebendazole, Pyrantel pamoate, Thiabendazole, Diethylcarbamazine, Ivermectin, Niclosamide, Praziquantel, Albendazole, Praziquantel, Rifampin, Amphotericin B, Melarsoprol, Eflornithine Metronidazole, Tinidazole, Miltefosine.

The term "resistance conferring protein" refers to any protein that renders a microorganism or microbe resistant to a drug. A resistance conferring protein may inactivate or degrade antimicrobial compounds (e.g.

beta-lactamase, aminoglycoside modifying proteins), may be an efflux pumps or other changes in the cell wall (e.g. poring alterations) that changes the permeability of the cell wall of the organism, or may be a mutation in target protein of the drug (e.g. ribosomal proteins or penicillin binding proteins (PBPs), reverse transcriptase, and/or protease), a protein that enables bypassing of a metabolic pathway may be a protein that protects the target site (e.g. quinolone resistance), or may be a target site-modifying protein. It should be understood that the list above is not exhaustive, any kind of drug resistance due to a protein may be detected by the present invention.

The term "beta-lactam antibiotic" is used to designate compounds with antibiotic properties containing a beta-lactam functionality. A betalactam ring (β-lactam) is a cyclic amide comprising a heteroatomic ring structure, consisting of three carbon atoms and one nitrogen atom. Non limiting examples of beta-lactam antibiotics useful in aspects of the invention include penicillins, cephalosporins, cephamycins, penems, carbapenems, and monobactams. Beta-lactam antibiotics are effective (in the absence of resistance) against a wide range of bacterial infections. The term "beta-lactam antibiotic" as used herein is considered to include any antibiotic undergoing mass or structural changes upon inactivation by an antibiotic resistant microorganism, provided said mass or structural change can be detected by mass spectrometry.

The terms "resistant" and "resistance", as used herein, refer to the phenomenon that a microorganism does not exhibit decreased viability or inhibited growth or reproduction when exposed to concentrations of the antimicrobial agent that can be attained with normal therapeutic dosage regimes in humans. It implies that an infection caused by this microorganism cannot be successfully treated with this antimicrobial agent.

The term "microorganism and/or microbe are used interchangeably, and refers to bacteria, yeast, fungi, intra- or extracellular parasites, and/or viruses and in particular to pathogenic microorganisms. In preferred aspects of the present invention, the term refers to pathogenic or opportunistic bacteria. These include both Gram-positive and Gram-negative bacteria. By way of Gram-negative bacteria, mention may be made of bacteria of the following non-limiting list of genera: *Pseudomonas, Escherichia, Salmonella, Shigella, Enterobacter, Klebsiella, Serratia, Proteus, Campylobacter, Haemophilus, Morganella, Vibrio, Yersinia, Acinetobacter, Branhamella, Neisseria, Burkholderia, Citrobacter, Hafnia, Edwardsiella, Aeromonas, Moraxella, Pasteurella, Providencia, Actinobacillus, Alcaligenes, Bordetella, Cedecea, Erwinia, Pantoea, Ralstonia, Stenotrophomonas, Xanthomonas* and *Legionella*. By way of Gram-positive bacteria, mention may be made of bacteria of the following non-limiting list of genera: *Enterococcus, Streptococcus, Staphylococcus, Bacillus, Listeria, Clostridium, Gardnerella, Kocuria, Lactococcus, Leuconostoc, Micrococcus, Mycobacteria* and *Corynebacteria*. By way of yeasts and fungi, mention may be made of yeasts of the following non-limiting list of genera: *Candida, Cryptococcus, Saccharomyces* and *Trichosporon*. By way of parasite mention may be made of parasites of the following non-limiting list of genera: ectoparasites, endoparasites, intercellular parasites, protozoa, mesoparasite, social parasites, plasmodium, entamoeba, giaria, toxoplasma, pinworm, schistosoma, strongyloides stercolasis, guinea worm, hookworm, tapeworm, sarcoptes scabiei, pediculus humanuss capitis, phtrirus pubis, ticks. By way of virus mention may be made of viruses of the following non-limiting list of genera: dsDNA viruses, ssDNA viruses, dsRNA viruses, (+)ssRNA viruses, (−)ssRNA viruses, ssRNA-RT viruses, dsDNA-RT viruses, such as for example polyomavirus, adenovirus, mosaic virus, hepadnavirus, geminivrius, arenavirus, circovirus, retrovirus, metavirus, pseudovirus, caulimorirus, herpesvirus, poxvirus, parvovirus, reovirus, picornavirus, togavirus, orthomyxovirus, rhabdovirus.

The term "mass spectrum", as used herein, refers to a plot having molecular mass or a function thereof (e. g., mass-to-charge ratio (m/z), ion mass, etc.) as the independent variable. The dependent variable is typically a quantitative measure, such as abundance, relative abundance, intensity, concentration, number of ions, number of molecules, number of atoms, counts/millivolt, counts, etc. For example, in the context of ions, a mass spectrum typically presents mass-to-charge ratio (m/z) as the independent variable, where m is the mass of the ion species and z is the charge of the ion species, and the dependent variable is most commonly an abundance of each molecular ion and/or its fragment ions. The term "ion" means an atom or a group of atoms that has acquired a net electric charge by gaining or losing one or more electrons or gaining or losing one or more protons. An ion can be formed in numerous manners, including by breaking up a molecule of a gas under the action of an electric current, of ultraviolet and certain other rays, and/or of high temperatures.

The term "lysate" as used herein refers to suspensions or fractions thereof, obtained by disruption or lysing of cells and/or other microorganisms such as viruses. The crude lysate contains all proteins, glycoproteins, polysaccharides, lipids, and nucleic acids. The lysate in aspects of the present invention may comprise whole cells or particles, but will essentially consist of parts of cells or particles or any fraction or mixtures thereof obtained after a lysis step. Lysate solutions, however, can include, without limitation, a solution of lysed cells and/or particles that is treated such that selected molecules are removed or rendered inactive. It follows that this solution remains substantially "crude" with respect to most purified constituents. For example, a cell lysate can be a solution of lysed cells that is treated with an agent that inactivates or removes polymerase inhibitors. In addition, a cell lysate can be a solution of lysed cells that is treated with an anti-coagulant. Any method can be used to lyse microorganisms in a sample. For example, osmotic shock, sonication, heating, physical disruption, microwave treatment, and enzymatic and/or alkaline lysis are methods that can be used to lyse microorganisms.

The terms "matrix material" and "MS matrix material", as used herein, are interchangeable and refer to a compound, whether in solution or solid, which may be used to form a matrix for use in mass spectrometry. For MS, the analyte must be embedded in a large excess of molecules which are well-absorbing at the wavelength at which the laser emits. These matrix molecules are generally small, organic compounds, mainly acids. Appropriate matrix materials for each type of laser used in MS are well known in the art and the term "MS matrix material" will be clearly understood by one of skill in the art. Without limiting the present invention, examples of commonly used matrix materials include sinapinic acid (SA), α-cyano-4-hydroxycinnamic acid (HCCA), 2,5-dihydroxybenzoic acid (DHB), 7-hydroxy-4-(trifluoromethyl)coumarin (HFMC), 3-Hydroxy Picolinic Acid (3-HPA), 5-(trifluoro-methyl)uracil, caffeic acid, succinic acid, anthranilic acid, 3-aminopyrazine-2-carboxylic acid, tetrakis(pentafluorfenyl)porfyrine and ferulic acid. Matrices are suitably dissolved in acetonitrile/water/formic acid (500: 500:1; v/v/v), or other suitable ratio's depending on the matrix used.

The term "sample", as used herein, refers to a substance that contains or is suspected of containing an analyte, such as a microorganism or drug resistance conferring protein to be characterized. A sample useful in a method of the invention can be a liquid or solid, can be dissolved or suspended in a liquid, can be in an emulsion or gel, and can be bound to or absorbed onto a material. A sample can be a biological sample, environmental sample, experimental sample, diagnostic sample, or any other type of sample that contains or is suspected to contain the analyte of interest. As such, a sample can be, or can contain, an organism, organ, tissue, cell, body fluid, biopsy sample, or fraction thereof. A sample useful in a method of the invention can be any material that is suspected to contain drug resistance conferring proteins. In a biological context, a sample can include biological fluids, whole organisms, organs, tissues, cells, microorganisms, culture supernatants, subcellular organelles, protein complexes, individual proteins, recombinant proteins, fusion proteins, viruses, viral particles, peptides and amino acids.

The term "quantifying", as used herein, refers to any method for obtaining a quantitative measure. For example, quantifying a microorganism can include determining its abundance, relative abundance, intensity, concentration, and/or count, etc. Quantifying an antimicrobial drug resistance conferring protein may encompass determining its expression level, its relative expression level to household proteins, and/or its concentration.

The present invention provides a fast and reliable diagnosis for drug resistance in microorganisms. It applies mass spectrometry to identify a resistance conferring protein in the microorganism sample. A well known resistance conferring protein is e.g. beta-lactamase that degrades or traps a beta-lactam such as penicillin, or aminoglycoside modifying proteins. A particular drug resistance is an resistance against an antibiotic, and especially resistance conferred by the so-called extended spectrum beta lactamases (ESBLs). Other antibiotic that may be degraded to confer resistance are penicillins, cephalosporins, cephamycins, and carbapenems, such as for example ceftazidime, cefotaxime, ceftriaxone, cefpodoxime, aztreonam, imipenem, meropenem and ertapenem. There are more than 900 different beta-lactamases known, each having its own activity and sensitivity. Clavulanic acid is a known inhibitor of beta-lactamases. Some beta lactamases are more sensitive to clavulanic acid then others. Such information is important for the diagnoses and for the subsequent treatment plan. Nowadays when more and more microorganisms are becoming resistant to antimicrobial drugs and specifically antibiotics, specific treatment of microorganism is extremely important to avoid further resistance. The resistance conferring protein may also be a mutation of an protein normally inhibited by the drug, such as gyrases, reverse transcriptase and/or proteases. The mutation overcomes the inhibition by the drug. The resistance conferring protein may also be a mutation in proteins affecting the activity of efflux pumps and/or content of proteins such that the permeability of the cell membrane is altered.

The microorganism may be a bacterium, fungus, virus, or parasite In a preferred embodiment of the present invention and/or embodiments thereof, the microorganism is a bacterium or a virus, more preferably a bacterium. In a preferred embodiment the microorganism is a fungus. In a another preferred embodiment the microorganism is a virus. In another preferred embodiment the microorganism is a fungus, or a parasite. The bacterium may be Gram-positive or Gram- negative or acid-fast bacteria (mycobacteria) and is preferably selected from the group consisting of *actinobacteria, firmicutes, tenericutes, aquificae, Deinoccos, fibrobacteres, chlorobi, bacteriodetes, fusobacteria, gemmatimonadetes, nitrospireae, planctomycetes, verrumicrobia, chlamydiae, protobacteria, spirochaetes, synergistetes, acidobacteria, chloroflexi, chrysiogenetes, cyanobacteria, deferribacteres, dictyoglomi, thermodesyslfobacteria*, and *thermotogae*.

In a preferred embodiment of the present invention and/or embodiments thereof, the microorganism is a pathogenic bacterium, preferably selected from the group consisting of *Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobactera, Mycoplasma, Neisseria, Pseudomonas, Rickettsia, Salmonella, Shigella, Staphylococcus, Streptococcus, Treponema, Tuberculosum, Vibrio*, and *Yersinia*. In a preferred embodiment of the present invention and/or embodiments thereof, the microorganism is selected from the group consisting of *Bordetella pertussis, Borrelia burgdorferi, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli, Francisella tularensis, Haemophilus influenzae, Helicobacter pylori, Legionella pneumophila, Leptospira interrogans, Listeria monocytogenes, Mycobacterium leprae, Mycobacterium tuberculosis, Mycobacterium ulcerans, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae*, and *Yersinia pestis*.

In a preferred embodiment of the present invention and/or embodiments thereof, the microorganism is a fungus. The fungus may be selected from the group consisting of Blastocladiomycota, Chytridiomycota, Glomeromycota, Microsporidia, Neocallimastigomycota, Dikarya (inc. Deuteromycota), Ascomycota , Pezizomycotina, Saccharomycotina, Taphrinomycotina, Basidiomycota, Agaricomycotina, Pucciniomycotina, Ustilaginomycotina, Subphyla incertae sedis, Entomophthoromycotina, Kickxellomycotina, Mucoromycotina, and Zoopagomycotina. In a preferred embodiment of the present invention and/or embodiments thereof, the microorganism is a pathogenic fungus, preferably selected from the group consisting of *Candida, Aspergillus, Cryptococcus, Histoplasma, Pneumocystis*, and *Tachybotrys*. In a preferred embodiment of the present invention and/or embodiments thereof, the microorganism is selected from the group consisting of *Candida albicans, Candida glabrata, Candida rugosa, Candida parapsilosis, Candida tropicalis, Candida dubliniensis, Aspergillus fumifatus, Aspergillus flavus, Aspergillus clavatus, Cryptococcus neoformans, Cryptococcus gatti, Histoplasma capsulatum , Pneumocystis jirovecii* and *Tachybotrys chartarum*.

In a preferred embodiment of the present invention and/or embodiments thereof, the microorganism is a parasite. The parasite may be selected from the group consisting of Flagellates (e.g., *Giardia lamblia*), Amoeboids (e.g., *Entamoeba histolytica*), Sporozoans (e.g., *Plasmodium knowlesi*), Apicomplexa, Myxozoa, Microsporidia, Ciliates (e.g., *Balantidium coli*), Subphylum Sarcomastigophora, Superclass Mastigophora (includes flagellates), Superclass Sarcodina, Superclass Opalinata, Subphylum Sporozoa (includes apicomplexans), Subphylum Cnidospora, Class Myxosporidea, Class Microsporidea, and Subphylum Ciliophora (includes ciliates). In a preferred embodiment of the present invention and/or embodiments thereof, the microorganism is a pathogenic parasite, preferably a protozoan, preferably selected from the group consisting of Amoebozoa, Excavata, and Chromalveolata. In a preferred embodiment of the present invention and/or embodiments thereof, the microorganism is selected from the group consisting of *Entamoeba histolytica, Plasmodium* (some of which cause malaria), and *Giardia lamblia, Trypanosoma brucei*, transmitted by the tsetse fly and the cause of African sleeping sickness.

In a preferred embodiment of the present invention and/or embodiments thereof, the microorganism is a virus. The virus may be selected from the group consisting of Adenoviruses, Herpesviruses, Poxviruses, Parvoviruses, Reoviruses, Picornaviruses, Togaviruses, Orthomyxoviruses, Rhabdoviruses, Retroviruses, and Hepadnaviruses. In a preferred embodiment of the present invention and/or embodiments thereof, the microorganism is a pathogenic virus preferably selected from the group consisting of HSV-1, HSV-2, Varicella zoster virus, EBV, CMV, smallpox virus, vaccinia virus, cowpox virus, human adenovirus, adenoassociated virus, erythrovirus, rotavirus, enterovirus, rhinovirus, Hepatitis A virus, Hepatitis B virus, Hepatitis C virus, rubella virus, flavivirusses, influenzavirus, lyssavirus, dengue virus, and HIV.

A suitable sample may be a body fluid or body tissue sample of a subject, i.e. a human, or animal subject, suspected of carrying a microorganism of which the f drug resistance is to be characterized. Suitable body fluid samples or clinical specimens may be blood, stool or urine sample. The sample may be a culture of a microorganism. Such cultures are preferably pure cultures, but do not need to be pure cultures necessarily. Alternatively, also fractions of culture media or direct clinical materials can be a source of the sample. In a preferred embodiment of the present invention and/or embodiments thereof, microorganism sample is a lysate of the microorganism, or a cell lysate. Several methods of sample preparation are known by skilled person, and the skilled person is enabled to select the most suitable method. In a preferred embodiment, the microorganism is lysed to release the content of the organism. Especially for Gram-negative bacteria and viruses lysis is preferred.

Suitable lysis agents are selected from the group comprising lytic enzymes such as lysozyme, lysins, lysostaphin, zymolase, cellulase, mutanolysin, glycanases, proteases, mannase, detergents such as CHAPS, triton X and SDS, beads such as glass, ceramic or steel beads.

It should be noted that lysis may be accomplished by sonication by e.g. ultrasound, cell bomb method by e.g. high pressure, cryopulverisation, and high shear mechanical methods such as rotor-stator disruptors, valve-type processors, fixed-geometry processors and fixed orifice and constant pressure processors.

In a preferred embodiment of the present invention and/or embodiments thereof, the microorganism sample is enriched in drug resistance conferring proteins. Suitable methods of enrichment comprise, purification of proteins by column chromatography, beads or column with antibodies recognizing resistance conferring proteins. Multiplex purification methods, i.e. enriching for more than one protein, is expressly envisioned for the present invention.

The digesting step provides a mix of peptides that are suitable for high resolution MS. Different mutations results in different peptides upon digestion, thereby differentiating between mutations in the same protein. Each protein will also render specific peptides upon digestion. Suitable proteases for the present invention and/or embodiments thereof are endoproteases, preferably endoproteases that cleave at a specific or known site of the protein. For the purpose of the present invention with specific or known cleaving site is meant that the protease will cleave at a predetermined location, preferably a location which is known. For example chymotrypsin preferentially cleaves peptide amide bonds where the carboxyl side of the amide bond is a large hydrophobic amino acid such as tyrosine, tryptophan, and phenylalanine. Proteases that cleave randomly, e.g. exoproteasess, are much less suitable for the present invention. Proteases are known to a skilled person, but may include trypsin, chymotrypsin, pepsin, C8, V8, LysN. In a preferred embodiment of the present invention and/or embodiments thereof, the cleavage action of the protease is known, and when the amino acid sequence of a protein is known, the cleavage profile may be predicted, including the mass of the peptides. Thus also for new drug resistance conferring proteins, and/or novel mutations, the protease digest may be determined once the amino acid sequence is known and the mass spectrum may be predicted. In a preferred embodiment of the present invention and/or embodiments thereof, more than one protease digestion may be used. Each different protease digestion results in different mix of peptides. For each different protease digest a mass spectrum may be acquired. The combined information from the different mass spectra may then determine the antimicrobial drug resistance. In a preferred embodiment of the present invention and/or embodiments thereof, the digesting step results in peptides in the range of 5-40 amino acids, more preferably in the range of 7-38 amino acids, more preferably in the range of 10-35 amino acids, more preferably in the range of 12-33 amino acids, more preferably in the range of 15-30 amino acids, more preferably in the range of 18-27 amino acids, more preferably in the range of 20-25 amino acids. The sensitivity of the MS depends on the m/z ratio of the peptide, if the charge z is high, the mass m may be higher. Peptides with a higher charge may have a higher nominal mass. In a preferred embodiment of the present invention and/or embodiments thereof, the digesting step results in peptides having a m/z ratio of 1-20 kDa, more preferably in the range of 1.5-15 kDa, more preferably in the range of 2-10 kDa, more preferably in the range of 3-8 kDa, and more preferably in the range of 4-6 kDa.

It is an important finding of the present inventors that the resistance conferring protein and/or a mutation of a protein can be measured very accurately by mass spectroscopy. Hence, the sample is prepared for mass spectrometry using generic mass spectrometry sample preparation protocols such as protein precipitation with organic solvents, solid-phase extraction (SPE), or liquid-liquid extraction (LLE) and affinity related methods. Approximately 1 µL of the prepared solution is used for the mass spectrometric analysis. The preparation of the mass spectrometric sample from the sample may be performed by methods known per se to one of skill in the art of mass spectrometry. Once the sample is mounted in the mass spectrometer, the mass spectrum of the sample is acquired by standard procedures that depend on the type of equipment and MS methods used. In a preferred embodiment of the present invention and/or embodiments thereof, the mass spectrum is acquired by high resolution MS. High resolution mass spectrometry (MS) provides the sensitivity to detect mutations in proteins. Suitably, the high resolution MS has a resolution of 1-10 ppm, more preferably of 1-5 ppm. Suitable mass spectrometers are Orbitrap, LC-qtrap, FT-ICR and Q-TOF. In a preferred embodiment the MS is not Maldi-TOF.

The present method is especially suited for identifying more than one resistance conferring protein. This provides an enormous advantage as in one measurement, several different types of drug resistance may be determined.

A further advantage of the present invention is the ability to quantify the drug resistance, e.g. by quantifying the resistance conferring protein. Preferably, the microorganism is quantified by quantifying in said samples one or more structural biomolecules or metabolites derived from said microorganism. This quantification is preferably followed by reference compounds such as stable isotope labeled peptides. In preferred embodiments, the structural biomolecules or metabolites are selected from the group consisting of nucleic acids, preferably (genomic) DNA. DNA is present as a single molecule inside the cell and can be quantified using for instance PCR-and/or DNA probing mediated technologies. In a preferred embodiment of the present invention and/or embodiments thereof, an internal standard is added to the sample of microorganism before the acquisition of the mass spectrum. The internal standard may consist of reference peptides having known amounts. Reference peptides with stable isotope labeled atoms such as the stable isotope, deuterium, $^{15}N$, or $^{13}C$, are particularly suitable.

In a preferred embodiment of the present invention and/or embodiments thereof the resistance conferring protein is selected form the group comprising β-lactamase, aminoglycoside modifying protein, gyrase, topoisomerase, rRNA methylase, penicillin binding protein such as PBP2a, or PBP2', clihydrofolate reductase, aminoacyl tRNA synthetase, RNA polymerase, dihydropteroate synthase, catalase-peroxidase, enoylACP reductase, alkyl hydroperoxidase, NADH dehydrogenase II.arabinosyl transferase, pyrazinamidase, reverse transcriptase, and protease. In a more preferred embodiment of the present invention and/or embodiments thereof the resistance conferring protein is selected form the group comprising β-lactamase, aminoglycoside modifying protein, gyrase, topoisomerase, rRNA methylase, penicillin binding protein such as PBP2a, or PBP2', dihydrofolate reductase, RNA polymerase, reverse transcriptase, and protease. In aspects described above, the invention provides in certain embodiments a method for the rapid diagnosis of microorganisms that comprise proteins conferring resistance to antimicrobial drugs. Especially in a hospital setting, this is highly needed because antibiotics and especially β-lactams including carbapenem antibiotics, aminoglycosides and quinolones are widely used in the empiric therapy for seriously ill patients with infections. Rapid detection of microbes resistant to antimicrobial drugs is at present extremely important. By rapid drug resistance detection the patient will be treated with the most appropriate antimicrobial drug therapy from the start. At present, empiric therapy or a wide range therapy is started and is sometimes switched at the moment the results of the susceptibility assays are reported. The methods of the present invention can be used for rapid detection of resistance conferring proteins. A method of the present invention can be performed using complex samples, including crude lysates or patient specimens. The method allows for the precise assessment of peptides that enables identification of the specific drug resistance conferring protein and/or mutation. It should be noted that this is in contrast to the MALDI-TOF detection of microorganism of the prior art. Most often the MS detection of the prior art detect a profile of several different, mostly ribosomal, proteins, wherein the profile is compared to reference spectra to determine the species. Usually in these cases, specific proteins are not identified; one only looks at the profile. Even if a certain type of protein is detected, such a beta-lactamase (Camera, and Hays Anal Bioanal Chem (2007) 389:1633-1638), there is no information about the kind of beta-lactamase. As there are more than 900 different beta-lactamases, the identification of a beta-lactamase without the information which beta-lactamase is not sufficient for correct treatment. Due to the differences in substrates hydrolyzing capacities it is crucial to know the exact nature of the protein in order to deduce the antimicrobial drug therapy not vulnerable to the specific protein detected.

The invention is further related to a kit of parts for characterizing the drug resistance of a microorganism comprising:
(a) a lysis agent for lysing a microorganism;
(b) a protease
(c) MS matrix materials.

In a preferred embodiment, the kit of parts of the present invention and/or embodiments thereof further comprises reference peptide, more preferably isotope labeled peptides. In a preferred embodiment the reference peptides are peptides from resistance conferring proteins, preferably the reference peptides include a mutation that confers resistance.

Suitable proteases for the present invention and/or embodiments thereof are endoproteases, preferably endoproteases that cleave at a specific or known site of the protein. For the purpose of the present invention with specific or known cleaving site is meant that the protease will cleave at a predetermined location, preferably a location which is known. For example chymotrypsin preferentially cleaves peptide amide bonds where the carboxyl side of the amide bond is a large hydrophobic amino acid such as tyrosine, tryptophan, and phenylalanine. Proteases that cleave randomly, e.g. exoproteasess, are much less suitable for the present invention. Preferred proteases may include trypsin, chymotrypsin, pepsin, C8, V8, LysN.

Suitable lysis agents are selected from the group comprising lytic enzymes such as lysozyme, lysins, lysostaphin, zymolase, cellulase, mutanolysin, glycanases, proteases, mannase, detergents such as CHAPS, triton X and SDS, beads such as glass, ceramic or steel beads.

It should be noted that lysis may be accomplished by sonication by e.g. ultrasound, cell bomb by e.g. high pressure, cryopulverisation, and high shear mechanical methods such as rotor-stator disruptors, valve-type processors, fixed-geometry processors and fixed orifice and constant pressure processors.

In a preferred embodiment, the kit of parts of the present invention and/or embodiments thereof further comprises software for analysis of the acquired mass spectrum.

Appropriate matrix materials for each type of laser used in MS are well known in the art. Suitable MS matrix materials include sinapinic acid (SA), α-cyano-4-hydroxycinnamic acid (HCCA), 2,5-dihydroxybenzoic acid (DHB), 7-hydroxy-4-(trifluoromethyl)coumarin (HFMC), 3-Hydroxy Picolinic Acid (3-HPA), 5-(trifluoro-methyl)uracil, caffeic acid, succinic acid, anthranilic acid, 3-aminopyrazine-2-carboxylic acid, tetrakis(pentafluorfenyl)porfyrine and ferulic acid. Matrices are suitably dissolved in acetonitrile/water/formic acid (500:500:1; v/v/v), or other suitable ratio's depending on the matrix used.

The invention is now exemplified by the following non-limiting examples.

EXPERIMENTAL SECTION

Gyrase Extraction 15 ml of an end-log phase culture in Todd Hewitt medium with an OD of 1.0 is centrifuged during 10 min. at 3.300×g at 4° C. The pellet is suspended in 1 ml of 25% sucrose in 10 mM Tris-HCl buffer (pH 7.5). Followed by 2 ml of 1.5 mM EDTA in 10 mM Tris-HCl buffer (pH 7.5) and mixed gently by hand. Subsequently, 15 µl (10× concentrated) Protea Prep Protease inhibitor (SP-820, Protea, Langdal, France) is added. The total volume is then transferred into 2 ml vials containing 18 glass beads (diameter 3mm) and subsequently shaken in a FastPrep system (FP 120 Bio 101 ThermoSavant, Holbrook, N.Y.) during 15 sec. at a speed of 6 m/s. This lysate is then centrifuged for 5 min. at 10.000× g at RT and the supernatants is frozen at −80° C. (5×0.5 ml).

Gyrase enrichment

To 50 µl of the frozen extract 950 µl cold acetone (−20° C.) was added and centrifuged for 10 min at 14.000 rpm by an Eppendorf centrifuge. The pellet was washed twice with 50 µl cold acetone and subsequently dried. The pellet was resuspended in 50 µl SDS-PAGE loading buffer. Next, 15 µl of this solution was diluted with 15 µl loading buffer. Twenty microliter of the diluted samples was loaded on to a 10% SDS-PAGE. The gel was stained with Novex® Colloidal Blue Staining (Invitrogen, Carlsbad, Calif.). The gel bands in the region of the height 116 KD were excised.

In-Gel Digestion

The gel bands were cut into small pieces and transferred into 1.5 mL Eppendorf tubes. The digestion was performed in Rapigest detergent solution (Waters Corporation, Milford, Mass.), according to the manufacturer's instructions. Briefly, the cut gel pieces were washed with water (10 min) and subsequently washed with a mixture of water/acetonitrile (1:1, v/v; for 10 min).

A sufficient volume of water/acetonitrile was added to shrink the gel pieces. The solution was removed and the gel pieces were rehydrated with 100 mM $NH_4HCO_3$ for 5 min. An equal volume of acetonitrile was added to the 100 mM $NH_4HCO_3$ solution, and it was incubated for 15 min. The washing solution was then removed and the gel pieces were dried in a Speedvac. The proteins were reduced with 10 mM DTT in 100 mM $NH_4HCO_3$ (45 min at 56° C.). After removing the reducing solution, proteins were alkylated in the dark with 50 mM iodoacetamide in 100 mM $NH_4HCO_3$ (30 min). The alkylation was stopped by removing the reaction solution and by washing the gel pieces with a mixture of water/acetonitrile (1:1, v/v), acetonitrile and acetonitrile/100 mM $NH_4HCO_3$. After the gel plug were dried in a Speedvac, 0.1% Rapigest in 50 mM $NH_4HCO_3$ was added and incubated at 37° C. for 10 minutes. Subsequently, the gel pieces were dried in a vacuum centrifuge. The gel pieces were rehydrated at 4° C. (45 min) with 10 ng trypsin (Promega, Madison, Wis.)/µl 50 mM NH₄HCO₃. Fifty microliter of 50 mM NH₄HCO₃ was added to completely cover the gel pieces. The digestion was carried out overnight at 37° C. Before starting the extraction, the supernatant was transferred to an Eppendorf tube. After adding to each sample 50 µl 1% trifluoroacetic acid it was incubated at 65° C. for 2 minutes. The supernatant was transferred into a new Eppendorf tube. To the gel pieces, 50 µl 50% acetonitrile and 50 µl 0.1% trifluoroacetic acid was added, the pieces were sonified for 2 minutes and subsequently incubated for 15 minutes at room temperature. The three resulting supernatants were pooled and dried in a vacuum centrifuge and redissolved in 50 µl 0.1% trifluoroacetic acid.

Mass Spectrometry

The completion of the digestion step was checked with reverse phase liquid chromatography and UV detection. For nanoLC LTQ-Orbitrap mass spectrometry measurements, ten microliters of peptide sample was injected on to a nanoliquid chromatography system (nanoLC Ultimate 3000; Thermo Scientific, Sunnyvale, Calif.). After preconcentration and washing of the sample on a C18 trap column (1 mm×300 µm i.d.), peptides were separated on a C18 PepMap column (250 mm×75 µm internal diameter) (Dionex, Amsterdam) using a linear 180 min gradient (3-25% acetonitrile/H20; 0.1% formic acid in 120 minutes and to 50% in 60 min) at a flow rate of 250 nL/min. The separation of the peptides was monitored by a UV detector (absorption at 214 nm). The nanoLC was coupled to a nanospray source of a linear ion trap Orbitrap (LTQ-Orbitrap) mass spectrometer (LTQ Orbitrap XL, Thermo Electron, Bremen, Germany). All samples were measured in a data dependent acquisition mode. The peptide masses are measured in a survey scan with a maximum resolution of 30,000 in the Orbitrap and an AGC (automatic gain control) setting of $1.00 \times 10^6$. To obtain a maximum mass accuracy, a prescan is used to keep the ion population in the Orbitrap for each scan approximately the same. During the high-resolution scan in the Orbitrap, the 5 most intense monoisotopic peaks in the spectra were fragmented and measured in the linear ion trap with normalized collision energy of 35% and an AGC setting of $1.00 \times 10^4$. The fragment ion masses are measured in the linear ion trap to have a maximum sensitivity and the maximum amount of MS/MS data.

Results

Figure 1:
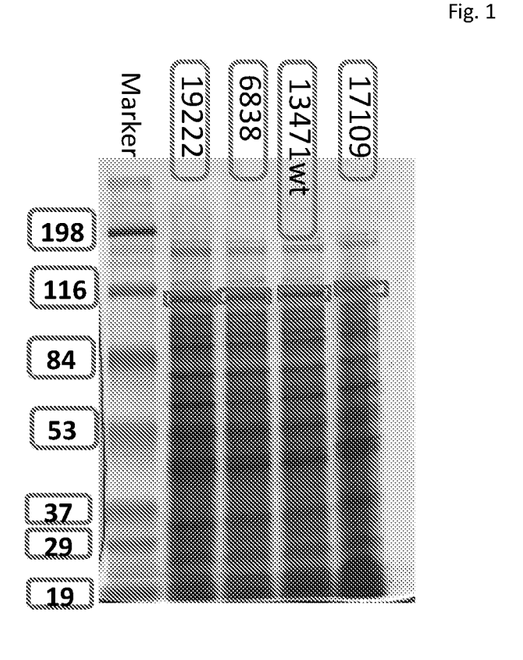
FIG. 1: gel electrophoreses of a sample of 4 different salmonella strains as indicated.
Figure 2:
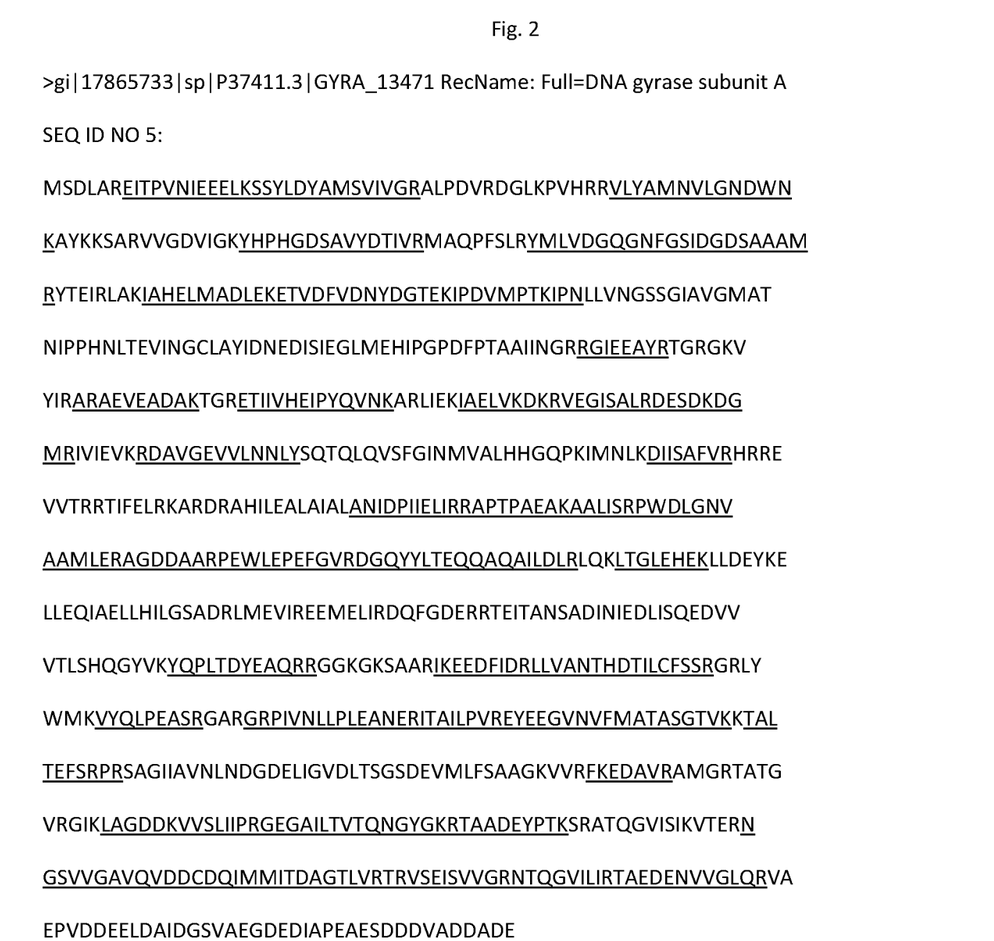
FIG. 2: Sequence of the gyrase of salmonella strain 13471 (wild type) wherein the sequenced parts are underlined.

Four different gyrases from salmonella strains were identified:

wild type (13471), coverage of the sequence was 54% (see FIG. 2). A specific peptide (amino acid 71-90) of the gyrase of the wild type gyrase was: SEQ ID NO: 1 GDVIG-KYHPH GDSAVYDTIV RMAQPFSLRY wherein underlined amino acids indicate mutation sites. MIC for ciprofloxacin is 0.03 µg/ml for wild type (13471).

Figure 3:
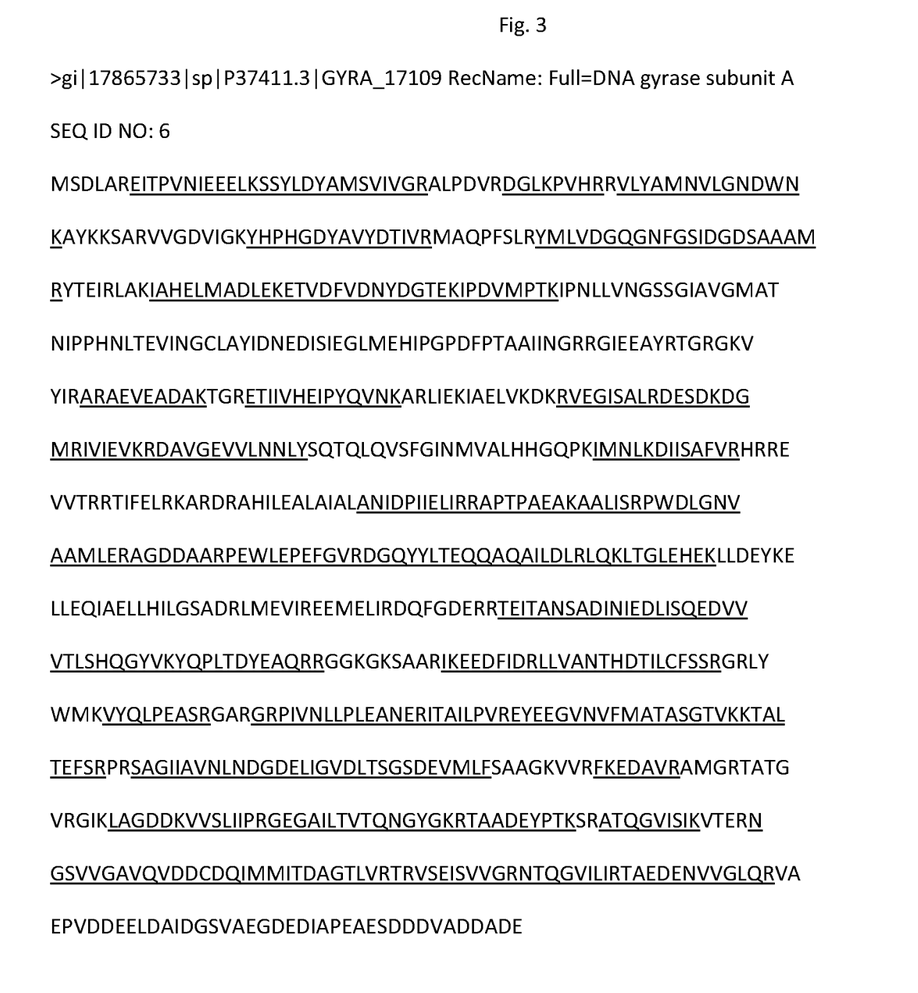
FIG. 3: Sequence of the gyrase of salmonella strain 17109 wherein the sequenced parts are underlined.

Salmonella strain 17109, coverage of the sequence was 64% (see FIG. 3). A specific peptide (amino acid 71-90) of the gyrase of the 17109 gyrase was: SEQ ID NO: 2 GDVIG-KYHPH GDYAVYDTIV RMAQPFSLRY wherein underlined amino acids indicate mutation sites. MIC for ciprofloxacin is 1.0 µg/ml for Salmonella strain 17109.

Figure 4:
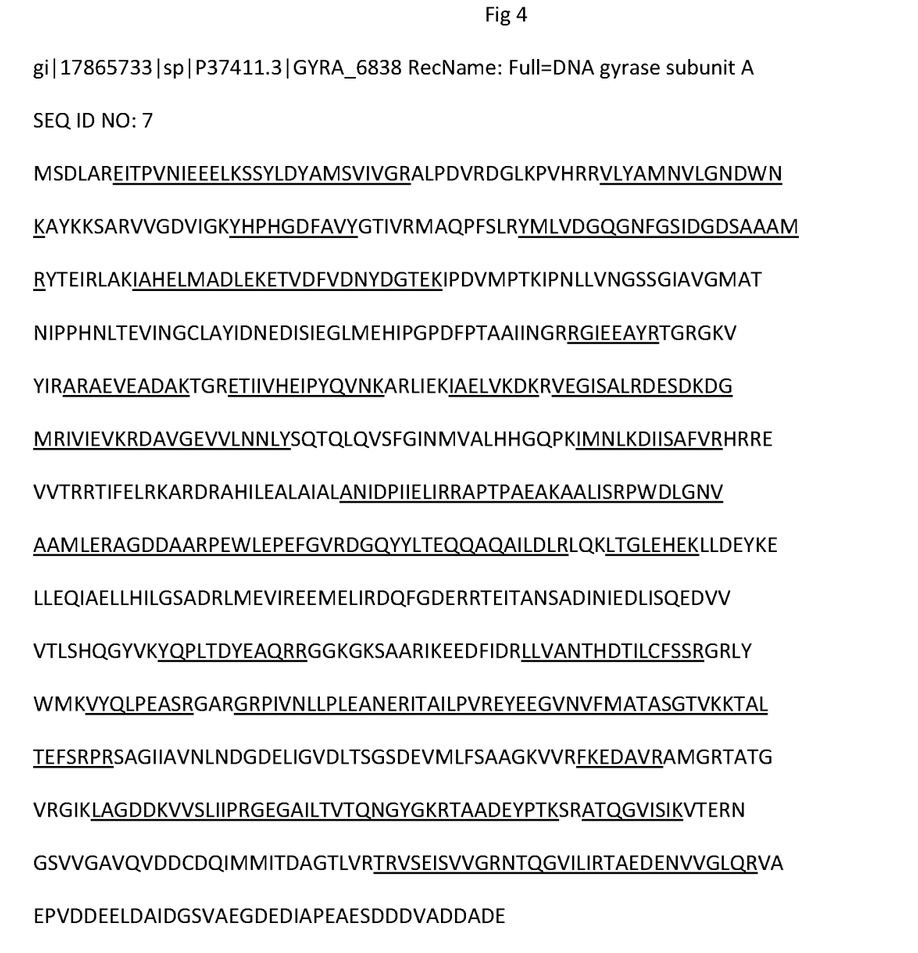
FIG. 4: Sequence of the gyrase of salmonella strain 6838 wherein the sequenced parts are underlined.

Salmonella strain 6836, coverage of the sequence was 50% (see FIG. 4). A specific peptide (amino acid 71-90) of the gyrase of the 6836 gyrase was: SEQ ID NO: 3 GDVIG-KYHPH GDFAVYGTIV RMAQPFSLRY wherein underlined amino acids indicate mutation sites. MIC for ciprofloxacin is 32 µg/ml for *Salmonella* strain 6836.

Figure 5:
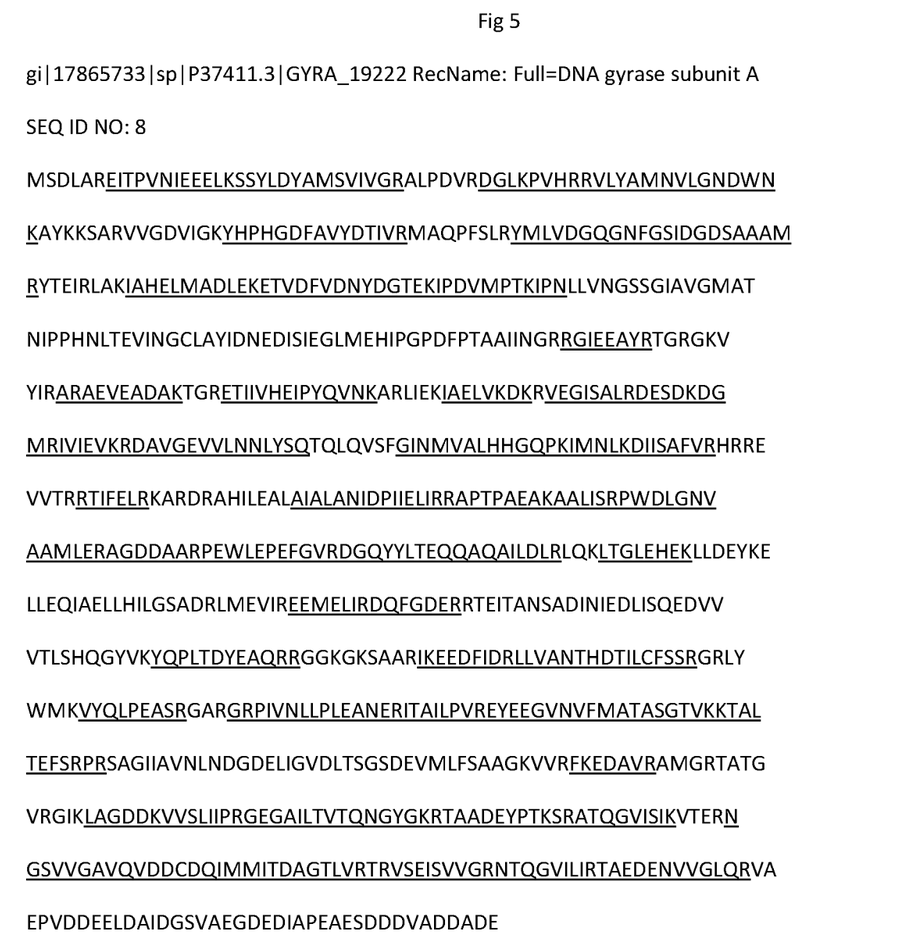
FIG. 5: Sequence of the gyrase of salmonella strain 19222 wherein the sequenced parts are underlined.

Salmonella strain 19222, coverage of the sequence was 62% (see FIG. 5). A specific peptide (amino acid 71-90) of the gyrase of the 19222 gyrase was: SEQ ID NO: 4 GDVIG-KYHPH GDFAVYDTIV RMAQPFSLRY wherein underlined amino acids indicate mutation sites. MIC for ciprofloxacin is 1.0 µg/ml for Salmonella strain 19222.

Conclusion

The substitution of the amino acids results in increase of the Minimum Inhibitory Concentration (MIC) for ciprofloxacin. It can be seen that one amino acid substitution results in a reduced susceptibility. Double mutations results in resistance to most members of the quinolone class. Being able to determine the exact resistance provides valuable information for the subsequent treatment. As can be seen, the different *Salmonella* strains have different MICs, which will have consequences for the treatment. Patients infected with Salmonella strain 17109 or strain 19222 will need treatment with a higher concentrations of ciprofloxacin, than patients infected with the WT strain. The present method enables doctors to tailor the antimicrobial treatment.

What is claimed is:

1. A method to detect resistance of a microorganism to an antimicrobial drug said method comprising the steps of:

(a) digesting a sample comprising proteins of a microorganism, wherein said sample is a lysate of a microorganism, a cell lysate, a crude lysate, or a patient specimen, wherein said sample contains or is suspected of containing a drug resistance conferring protein, resulting in a mix of peptides, representing a protein digest, wherein different amino acid substitutions in the sequence of the protein result in different peptides upon digestion and wherein each protein renders specific peptides upon digestion, such that when the cleavage action of the protease and the amino acid sequence of a protein are known, the cleavage profile of different peptides in the protein digest including the mass of the different peptides may be predicted;

(b) acquiring a mass spectrum of the mix of peptides obtained in step (a) by high resolution mass spectrometry at a resolution of 1-10 ppm, wherein said mass spectrum provides information on whether said drug resistance conferring protein is present, on the type of drug resistance conferring protein and on amino acid substitutions in the sequence of the drug resistance conferring protein to thereby allow for the precise assessment of peptides and identification of the specific drug resistance conferring protein and/or amino acid substitution mutations therein;

(c) identifying from the mass spectrum under (b) a resistance conferring protein by detecting an amino acid substitution mutation in said resistance conferring protein, using reference peptides from resistance conferring proteins wherein said reference peptides include an amino acid substitution mutation that confers resistance to thereby determine the resistance of the microorganism.

2. The method according to claim 1 wherein the microorganism sample is enriched in the drug resistance conferring protein.

3. The method according to claim 1 wherein the digesting step results in peptides in the range of 5-40 amino acids.

4. The method according to claim 1 wherein more than one resistance conferring protein is identified.

5. The method according to claim 1 wherein an internal standard is added to the sample of microorganism before the acquisition of the mass spectrum.

6. The method according to claim 1 wherein the microorganism is quantified by quantifying the resistance conferring protein.

7. The method according to claim 1 wherein the resistance conferring protein is selected from the group consisting of β-lactamase, aminoglycoside modifying protein, mutated gyrase, topoisomerase, rRNA methylase, PBP2a of PBP2', dihydrofolate reductase, aminoacyl tRNA synthetase, RNA polymerase, dihydropteroate synthase, catalase-peroxidase, enoylACP reductase, Alkyl hydroperoxidase, NADH dehydrogenase, arabinosyl transferase, and pyrazinamidase.

8. The method according to claim 1, wherein the sample of a microorganism comprising proteins is digested with an endoprotease.

9. The method according to claim 1, wherein said high resolution mass spectrometry involves the use of FT-ICR or Q-TOF.

10. The method according to claim 1, wherein said high resolution mass spectrometry does not involve the use of MALDI-TOF.

* * * * *